United States Patent [19]

Pedersen et al.

[11] Patent Number: 5,698,749
[45] Date of Patent: Dec. 16, 1997

[54] CATALYSTS FOR THE HYDROGENATION OF AQUEOUS MALEIC ACID TO 1,4-BUTANEDIOL

[75] Inventors: S. Erik Pedersen, Hurricane, W. Va.; John G. Frye, Jr., Richland, Wash.; Thomas G. Attig, Aurora; John R. Budge, Beachwood, both of Ohio

[73] Assignee: The Standard Oil Company, Cleveland, Ohio

[21] Appl. No.: 524,195

[22] Filed: Sep. 6, 1995

(Under 37 CFR 1.47)

[51] Int. Cl.⁶ .................... C07C 29/149; C07D 307/08
[52] U.S. Cl. ............................ 568/864; 549/508
[58] Field of Search ................... 549/508; 568/864

[56] References Cited

U.S. PATENT DOCUMENTS

| | | | |
|---|---|---|---|
| 3,948,805 | 4/1976 | Michalczyk et al. | 252/447 |
| 4,096,156 | 6/1978 | Freudenberger et al. | 260/343.6 |
| 4,550,185 | 10/1985 | Mabry et al. | 549/508 |
| 4,609,636 | 9/1986 | Mabry et al. | 549/508 |
| 4,973,717 | 11/1990 | Williams | 549/508 |
| 4,985,572 | 1/1991 | Kitson et al. | 549/326 |
| 5,473,086 | 12/1995 | Budge et al. | 549/508 |

FOREIGN PATENT DOCUMENTS

| | | |
|---|---|---|
| 1534232 | 11/1978 | United Kingdom . |
| 1551741 | 8/1979 | United Kingdom . |

*Primary Examiner*—Bernard Dentz
*Attorney, Agent, or Firm*—David P. Yusko; David J. Untener

[57] ABSTRACT

Maleic acid, maleic anhydride or other hydrogenatable precursor are catalytically hydrogenated to 1,4-butanediol and tetrahydrofuran. It has been discovered that high yields of 1,4-butanediol are achieved when the hydrogenation catalyst comprises at least one noble metal of Group VIII of the Periodic Table and at least one of rhenium, tungsten or molybdenum on a carbon support wherein the carbon support has been contacted with an oxidizing agent prior to the deposition of the metals. This hydrogenation catalyst is prepared by the steps of (i) oxidizing the carbon support by contacting the carbon support with an oxidizing agent, (ii) impregnating in one or more impregnation steps comprising contacting the carbon support with a source of Group VIII metal and at least one metal selected from the group consisting of rhenium, tungsten and molybdenum being in at least one solution, (iii) after each impregnation step, drying at a temperature under about 150° C. the impregnated carbon support to remove solvent, (iv) heating the impregnated carbon support at a temperature of about 100° C. to about 350° C. under reducing conditions.

13 Claims, No Drawings

CATALYSTS FOR THE HYDROGENATION OF AQUEOUS MALEIC ACID TO 1,4-BUTANEDIOL

BACKGROUND OF THE INVENTION

1. Field of the Invention

This invention relates to an improved process for the hydrogenation of maleic acid, maleic anhydride or other hydrogenatable precursor to 1,4-butanediol and tetrahydrofuran. The process is characterized by the use of a catalyst comprising at least one noble metal of Group VIII of the Periodic Table and at least one of rhenium, tungsten or molybdenum on a carbon support, wherein the carbon support has been contacted with an oxidizing agent prior to the deposition of the metals. The process is also characterized by higher overall activity to reaction products and/or by higher yields of 1,4-butanediol with minimal formation of gamma-butyrolactone by-products.

2. Description of the Prior Art

It is well known that tetrahydrofuran, gamma-butyrolactone and 1,4-butanediol are obtained by the catalytic hydrogenation of maleic anhydride and related compounds. Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants. 1,4-butanediol (a.k.a. 1,4-butylene glycol) is useful as a solvent, a humectant, an intermediate for plasticizers and pharmaceuticals, a cross-linking agent for polyurethane elastomers, a precursor in the manufacture of tetrahydrofuran, and is used to make terephthalate plastics.

Of particular interest in the instant invention are hydrogenation catalysts comprising a Group VIII noble metal and at least one metal selected from the group consisting of rhenium, tungsten and molybdenum on a carbon support. British Patent No. 1,534,232 teaches the hydrogenation of carboxylic acids, lactones or anhydrides using a hydrogenation catalyst consisting of palladium and rhenium on a carbon support. U.S. Pat. Nos. 4,550,185 and 4,609,636 teach a process of making tetrahydrofuran and 1,4-butanediol by hydrogenating maleic acid, maleic anhydride or other hydrogenatable precursor in the presence of catalyst comprising palladium and rhenium on a carbon support wherein the palladium and rhenium were present in the form of crystallites having an average palladium crystallite size of about 10 to 25 nm and an average rhenium crystallite size of less than 2.5 nm. The preparation of this catalyst is characterized by the deposition and reduction of the palladium species on the carbon support followed by the deposition and reduction of the rhenium species on the palladium impregnated carbon support.

U.S. Pat. No. 4,985,572 teaches a process for the catalytic hydrogenation of a carboxylic acid or an anhydride thereof to the corresponding alcohol and/or carboxylic acid ester using a catalyst comprising rhenium and an alloy of palladium and silver on a carbon support. The preparation of this catalyst is characterized by the simultaneous deposition of palladium and silver on the carbon support followed by a high temperature (600° C.) heat treatment to alloy the catalyst. Rhenium was then deposited on the alloy impregnated carbon support. The resulting catalyst was then reduced.

Generally, in the hydrogenation of maleic acid, maleic anhydride or other hydrogenatable precursor the above discussed catalysts have the propensity to produce more tetrahydrofuran and gamma-butyrolactone than 1,4-butanediol. An object of this invention is a process and a more active catalyst which will maximize 1,4-butanediol production.

SUMMARY OF THE INVENTION

Maleic acid, maleic anhydride or other hydrogenatable precursor are catalytically hydrogenated to 1,4-butanediol and tetrahydrofuran. It has been discovered that high yields of 1,4-butanediol are achieved when the hydrogenation catalyst comprises at least one noble metal of Group VIII of the Periodic Table and at least one of rhenium, tungsten or molybdenum wherein the carbon support has been contacted with an oxidizing agent prior to the deposition of the metals. This hydrogenation catalyst is prepared by the steps of (i) oxidizing the carbon support by contacting the carbon support with an oxidizing agent, (ii) impregnating in one or more impregnation steps comprising contacting the carbon support with a source of Group VIII metal and at least one metal selected from the group consisting of rhenium, tungsten and molybdenum, (iii) after each impregnation step, drying at a temperature under about 150° C. the impregnated carbon support to remove solvent, and (iv) heating the impregnated carbon support at a temperature of about 100° C. to about 350° C. under reducing conditions.

DETAILED DESCRIPTION OF THE INVENTION

A hydrogenatable precursor is catalytically hydrogenated to provide high yields of 1,4-butanediol and smaller yields of tetrahydrofuran with minimal gamma-butyrolactone formation.

Reactants

At least one hydrogenatable precursor is reacted with a hydrogen containing gas in the presence of the catalyst.

As used herein a "hydrogenatable precursor" is any carboxylic acid or anhydride thereof, carboxylic acid ester, lactone or mixture thereof which when hydrogenated produces 1,4-butanediol. Representative hydrogenatable precursors include maleic acid, maleic anhydride, fumaric acid, succinic acid, malic acid, dimethyl succinate, gamma-butyrolactone or mixtures thereof. The preferred hydrogenatable precursors are maleic acid, maleic anhydride, gamma-butyrolactone and mixtures thereof.

Typically, the hydrogen ($H_2$) containing gas is commercially pure hydrogen. However, the hydrogen containing gas in addition to hydrogen ($H_2$) may also contain nitrogen ($N_2$), any gaseous hydrocarbon (e.g. methane), as well as gaseous oxides of carbon, (e.g. carbon monoxide, carbon dioxide).

Catalyst

The catalyst employed in the instant invention comprises at least one a noble metal of Group VIII of the Periodic Table of Elements and at least one metal selected from the group consisting of rhenium, tungsten and molybdenum supported on a carbon support. The Group VIII metals are palladium, platinum, rhodium, ruthenium, osmium, and iridium. The preferred Group VIII metals are palladium, platinum, rhodium and ruthenium. The most preferred Group VIII metal is palladium.

The carbon support used in this invention are high surface area carbons and should have a BET surface area of at least 200 $m^2/g$, and preferably be in the range of 500–1500 $m^2/g$. The carbon support is generally obtained from commercially available activated carbons commonly derived from either wood or coconut shell.

The catalyst Composition comprises about 0.1 to about 20 weight percent of the Group VIII metal, preferably about 1 to about 10 weight percent of the Group VIII metal, and about 0.1 to about 20 weight percent of at least one of rhenium, tungsten or molybdenum, preferably about 1 to about 10 weight percent of at least one of rhenium, tungsten or molybdenum. The weight ratio of the Group VIII metal to the total of rhenium, tungsten and molybdenum is between 10:1 and 1:10. The catalyst composition may also be further modified through the incorporation of one or more additional metals. Preferred additional metals are selected from Groups IA, IIA and IB of the Periodic Table.

In the instant invention the carbon support is oxidized by contacting the carbon support, prior to deposition of the metals, with a oxidizing agent. Catalysts prepared in this manner show a dramatic improvement in activity and selectivity over catalysts prepared with non-oxidized carbon support. A number of oxidizing agents such as nitric acid, hydrogen peroxide, sodium hypochlorite, ammonium persulfate, perchloric acid, and oxygen may be effective in this process. Liquid phase oxidizing agents at elevated temperatures (between about 60° C. an about 100° C.) are preferred. Concentrated nitric acid at elevated temperatures has been found to be especially effective for this procedure. Gaseous phase oxidizing agents include any oxygen-containing gas, e.g. air. Gaseous oxidizing agents are contacted with the carbon support at temperatures of about 200° C. or greater and at pressures of about atmospheric or greater.

In preparing the catalysts of this invention, the metals are deposited on the carbon support by impregnation of the carbon support, either in single or multiple impregnation steps, with a solution or solutions containing at least one Group VIII compound. As used herein, impregnation of the carbon support means to cause the carbon support to be filled, imbued, permeated, saturated or coated. The impregnated carbon support is then dried after each impregnation step. The solution(s) of metal-containing compounds used to impregnate the carbon support may optionally contain complexing agents to help solubilize one or more of the metal compounds. The carrier solvent is removed by drying after each impregnation step. Drying temperatures are between about 100° C. and about 150° C.

The solution(s) of metal-containing compounds can impregnate the carbon support by immersing or suspending the support material in the solution or by spraying the solution onto the carbon. The solution containing the Group VIII compound is typically an acidic aqueous medium containing $HNO_3$ and an amount of Group VIII metal compound to yield a catalyst product with the requisite amount of Group VIII metal. The Group VIII metal compound may be a chloride, nitrate, carbonate, carboxylate, acetate, acetyl acetonate, or amine. The solution(s) containing the rhenium, tungsten or molybdenum compound is typically an aqueous one containing an amount of rhenium, tungsten or molybdenum compound to yield a catalyst product with the requisite amount of at least one of these three metals. Where rhenium is used in the catalyst the rhenium compound is typically perrhenic acid, ammonium perrhenate or an alkali metal perrhenate.

After impregnation of the carbon support with palladium, silver, and rhenium and drying, the catalyst (i.e. the impregnated carbon support) is activated by heating under reducing conditions at a temperature of 120°–700° C., preferably 150°–300° C. Hydrogen, or a mixture of hydrogen and nitrogen, in contact with the catalyst, is typically employed for the catalyst reduction.

The Process

The typical method for carrying out the process comprises (a) reacting n-butane or benzene in an oxygen-containing gas in the presence of a vanadium/phosphorus mixed oxide catalyst to oxidize in the vapor-phase the n-butane or benzene to maleic anhydride, (b) collecting the maleic anhydride by a water quench to produce maleic acid in an aqueous solution at a concentration of about 40 weight percent, (c) reacting the solution obtained in (b) with a hydrogen-containing gas in the presence of the hydrogenation catalyst, and (d) recovering and purifying the reaction products by distillation.

Preferably, oxidation step (a) is operated at a temperature of about 300° C. to 600° C. and a pressure of about 0.5 to 20 atmospheres (50 to 2000 kPa) and hydrogenation step (c) is run at a temperature of about 50° C. to 350° C., and a hydrogen pressure of about 20–400 atmospheres, more preferably 80 to 200 atmospheres, with hydrogen to hydrogenatable precursor ratios ($H_2/P$) of between 5 to 1 and 1000 to 1 and contact times of 0.1 minute to 20 hours.

The liquid phase hydrogenation of this invention can be run using conventional apparatus and techniques in a stirred-tank reactor or in a fixed-bed reactor. The amount of catalyst required will vary widely and is dependent upon a number of factors such as reactor size and design, contact time and the like. Hydrogen is fed continuously, generally in considerable stoichiometric excess with no inert diluent gases. Unreacted hydrogen can be returned to the reactor as a recycle stream. The precursor solution, e.g., maleic acid solution, is fed at concentrations ranging from dilute solutions to near the maximum solubility level, typically about 50 weight percent.

The reaction products, 1,4-butanediol, tetrahydrofuran, gamma-butyrolactone or mixtures thereof are advantageously separated by fractional distillation. The gamma-butyrolactone may also be recycled to the hydrogenation reactor.

Using the process of this invention, more specifically using the hydrogenation catalyst described herein, maleic acid is converted virtually quantitatively in a simple reaction. The yields of 1,4-butanediol and tetrahydrofuran achieved are about 80 mole percent or greater, typically about 90 mole percent or greater, with a majority portion of the yield being 1,4-butanediol. The formation of non-utilizable by-products is slight.

Reaction by-products may include n-butanol, n-butyric acid, n-propanol, propionic acid, methane, propane, n-butane, carbon monoxide, and carbon dioxide.

SPECIFIC EMBODIMENTS

The following embodiments are to be construed as merely illustrative, and not limitative of the remainder of the disclosure in any way.

Example 1

5% Pd/5% Re on oxidized carbon 100 g of 30×70 mesh activated carbon (ACL40, produced by CECA S.A. of France and sold in the United States by Atochem North America Inc., hereinafter referred to as "CECA ACL40") was stirred with an excess of concentrated nitric acid (69–71% $HNO_3$) at 80° C. for about 18 hours. After cooling the product was recovered by filtration and washed several times with an excess of water followed by oven drying at 120° C.

25.00 g of the oxidized carbon was treated with 120 g of an aqueous solution containing 1.90 g $NH_4ReO_4$ and 18.12 g $Pd(NO_3)_2$ solution (7.26% Pd). The resulting slurry was evaporated to dryness on a "roto-vac" and oven dried at 120° C. The product was now reduced in hydrogen at 200° C. The ramp rate was 1°/min with a hold time of 5 hours at 200° C.

8.00 g of the reduced catalyst (nominally 5% Pd/5% Re on carbon) was mixed with 100.0 g of 30% aqueous maleic acid and the mixture was placed in an autoclave. The autoclave was purged three times with 2500 psig $H_2$ at room temperature followed by an increase in the temperature to 160° C. at a stirring rate of 1000 rpm while maintaining the pressure at 2500 psig. The reactants were kept under those conditions for 9.5 hours and then allowed to cool to ambient temperature. The products were analyzed by gas chromatography and showed 100% maleic conversion with 1,4-butanediol (BDO) selectivity of 86.9% as well as 5.2% tetrahydrofuran (THF), 2.4% gamma-butyrolactone (GBL) and 4.6% n-butanol.

Comparative Example A

5% Pd/5% Re on carbon—not oxidized

The procedure in Example 1 was repeated using the same activated carbon but without the nitric acid treatment. When this catalyst was tested under conditions identical to those used in Example 1, the selectivity to BDO was only 0.3% while the selectivity to GBL, THF, and n-butanol were 84.5%, 12.0% and 2.0% respectively.

Example 2

3% Pd/3% Ag/6% Re on oxidized carbon 100 gms. of CECA ACL40 activated carbon extrudate was placed in a 1 Liter, 3-neck flask equipped with a mechanical stirrer, a liquid addition funnel, and a glass thermowell. A ⅛ " dia. Type K thermocouple was inserted into the thermowell and was connected to a temperature control box. The temperature control box was in turn connected to a heating mantle within which the flask rested. The mechanical stirrer was turned on at a low RPM and approx. 450 ml of concentrated nitric acid (69–71% $HNO_3$) was dropwise to the flask over a period of about 2 hrs. After the addition of the acid was complete, the addition funnel was removed and replaced with a reflux condenser. The setpoint of the temperature controller was slowly increased to 80° C. The contents of the flask were allowed to continue stirring slowly at the 80° C. temperature overnight. Following the nitric acid treatment, the carbon was thoroughly washed with distilled water, then dried overnight at 100° C.

50 cc (23.85 gms.) of the oxidized carbon were used as the catalyst support for this catalyst preparation. An impregnation solution was prepared by placing 11.31 gms. of $Pd(NO_3)_2$ soln. (7.70% Pd by wt.), 1.34 gms. of $AgNO_3$, and 3.37 gms. of $HReO_4$ soln. (52.63% Re by wt.) in a 25 ml volumetric flask along with enough acetonitrile to make the solution volume up to 25 ml. The solution density was 1.109 gms./cc. 25.39 gms. of the above solution were used to impregnate the 50 cc of the oxidized carbon extrudate. Following impregnation of the carbon with the metals solution, the carbon was placed in an oven at 90° C. to dry. The metals loading in this catalyst preparation was 0.016 gm. Pd/cc of support, 0.016 gm. Ag/cc of support, and 0.032 gm. Re/cc of support.

20 cc (11.79 gms.) of the dried, metals-impregnated oxidized carbon catalyst preparation was loaded into a Hastelloy C reactor tube (0.62"O.D.×0.55"I.D.). The catalyst was initially reduced at 280° C. for 5 hrs. under a flowing stream of hydrogen (at atmospheric pressure). The catalyst was started up under the following conditions:

System Pressure=1300 PSIG $H_2$:Maleic Acid Feed Ratio=65:1

Liquid Feed Composition=400 gms.Maleic Acid/Liter

Liquid Hourly Space Velocity(LHSV)=0.38

Reactor Setpoint Temperature=180° C.

Under the above process conditions the following product selectivities were observed:

| | |
|---|---|
| Tetrahydrofuran (THF) = | 13.9% |
| Gamma-butyrolactone (GBL) = | 1.6% |
| Butanediol (BDO) = | 46.1% |
| n-Butanol (BuOH) = | 30.6% |

In order to test the inherent activity of the catalyst, the LHSV is usually increased and/or the reactor setpoint temperature decreased until a significant-increase in gamma-butyrolactone is observed in the product solution (GBL breakthrough occurs). For this catalyst, GBL breakthrough was observed at a setpoint temperature of 150° C. and an LHSV=0.55. The product selectivities observed under those conditions were as follows:

| | |
|---|---|
| Tetrahydrofuran (THF) = | 4.7% |
| Gamma-butyrolactone (GBL) = | 4.2% |
| Butanediol (BDO) = | 84.8% |
| n-Butanol (BuOH) = | 3.9% |

Comparative Example B

4% Pd/4% Ag/8% Re on carbon—not oxidized 120 cc (51.8 gms.) of CECA ACL40 activated carbon extrudate was used as the catalyst support in this catalyst preparation. An impregnation solution was prepared by placing 27.8 gms. of $Pd(NO_3)_2$ solution (7.70% Pd by wt.), 3.3 gms. of $AgNO_3$, and 8.3 gms. of $HReO_4$ solution (52.6% Re by wt.) in a 50 ml volumetric flask with enough acetonitrile to make the solution volume up to 50 ml. The solution density was 1.1828 gms./cc. 57.2 gms. of the solution was used to impregnate the 120 cc of activated carbon extrudate. Following impregnation with the metals solution, the carbon was placed in an oven at 120° C. to dry. The metals loading used in this catalyst preparation was 0.017 gm. Pd/cc of support, 0.017 gm. Ag/cc of support, and 0.035 gm.Re/cc of support. This is the same metals loading as the catalyst used in Example 2.

20 cc (10.67 gms.) of the above dried, metals-impregnated carbon catalyst preparation was loaded into a Hastelloy C reactor tube (0.62"O.D.×0.55"I.D.). The catalyst was initially reduced at 280° C. for 5 hrs. under a flowing stream of hydrogen (at atmospheric pressure). The catalyst was started up under the following conditions:

System Pressure=1300 PSIG

H$_2$:Maleic Acid Feed Ratio=65:1

Liquid Feed Composition=400 gms. Maleic Acid/Liter

Liquid Hourly Space Velocity(LHSV)=0.38

Reactor Setpoint Temperature=180° C.

Under the above process conditions, the following product selectivities were observed:

| | |
|---|---|
| Tetrahydrofuran (THF) = | 44.3% |
| Gamma-butyrolactone (GBL) = | 1.4% |
| Butanediol (BDO) = | 30.7% |
| n-Butanol (BuOH) = | 18.2% |

In order to test the inherent activity of the catalyst, the LHSV is usually increased and/or the reactor setpoint temperature decreased until a significant increase in gamma-butryolactone is observed in the product solution (gamma-butryolactone breakthrough occurs). For this catalyst, GBL breakthrough was observed at a setpoint temperature of 175° C. and an LHSV=0.55. The product selectivities observed under those conditions were as follows:

| | |
|---|---|
| Tetrahydrofuran (THF) = | 41.2% |
| Gamma-butyrolactone (GBL) = | 12.7% |
| Butanediol (BDO) = | 36.0% |
| n-Butanol (BuOH) = | 6.4% |

Example 3

3% Pd/3% Ag/6% Re on oxidized carbon

Two 100 gram batches of CECA ACL40 activated carbon extrudate were oxidized as per the procedure described in Example 2 above. 350 cc (166.17 gms.) of the oxidized carbon were used as the catalyst support for this catalyst preparation. An impregnation solution was prepared by placing 112.45 gms. of Pd(NO$_3$)$_2$ soln. (7.70% Pd by wt.), 13.33 gms. of AgNO$_3$, and 33.50 gms. of HReO$_4$ (52.63% Re by wt.) in a 250 ml volumetric flask along with enough acetonitrile to make the solution up to 250 ml. The solution density was 1.1006 gms./cc. 177.39 gms. of the above solution were used to impregnate the 350 cc of oxidized carbon extrudate. Following impregnation of the carbon with the metals solution, the carbon was placed in an oven at 90° C. to dry. The metals loading in this catalyst preparation per cc of carbon support were 0.016 gm. Pd/cc, 0.016 gm. Ag/cc, and 0.032 gm. Re/cc.

40 cc (23.36 gms.) of the dried, metals-impregnated oxidized carbon catalyst preparation was loaded into a Hastelloy C reactor tube (0.745" O.D.×0.475" I.D.) and subsequently into the recycle reactor rig. The catalyst was initially reduced at 280° C. for 5 hrs. under a flowing stream of hydrogen (at atmospheric pressure). The catalyst was started up under the following conditions:

System Pressure=2500 PSIG

H$_2$:Maleic Acid Feed Ratio=65:1

Liquid Feed Composition=400 gms. Maleic Acid/Liter

Liquid Hourly Space Velocity (LHSV)=0.55

Reactor Setpoint Temperature=180° C.

Under the above process conditions the following product selectivities were observed:

| | |
|---|---|
| Tetrahydrofuran (THF) = | 8.5% |
| Gamma-butyrolactone (GBL) = | 0.2% |
| Butanediol (BDO) = | 55.4% |
| n-Butanol (BuOH) = | 29.6% |

In order to test the inherent activity of the catalyst, the LHSV is usually increased and/or the reactor setpoint temperature decreased until a significant increase in gamma-butyrolactone is observed in the product solution (GBL breakthrough occurs). In this case, in order to obtain a side by side comparison with the catalyst in Comparative Example C, the setpoint temperature was reduced to 150° C. and the LHSV was maintained at 0.55. The product selectivities observed under those conditions were as follows:

| | |
|---|---|
| Tetrahydrofuran (THF) = | 2.1% |
| Gamma-butyrolactone (GBL) = | 0.1% |
| Butanediol (BDO) = | 90.2% |
| n-Butanol (BuOH) = | 6.6% |

As can be seen from the above table, no significant GBL breakthrough has occurred for this catalyst under this set of conditions. In order to further probe the activity of this catalyst, the LHSV was maintained at 0.55 while the setpoint temperature was reduced to 140° C. The product selectivities observed under those conditions were as follows:

| | |
|---|---|
| Tetrahydrofuran (THF) = | 1.6% |
| Gamma-butyrolactone (GBL) = | 0.3% |
| Butanediol (BDO) = | 92.8% |
| n-Butanol (BuOH) = | 4.6% |

As a further example of this catalyst's activity and selectivity, the setpoint temperature was again increased to 150° C. and the LHSV was increased to 0.75. The product selectivities observed under those conditions were as follows:

| | |
|---|---|
| Tetrahydrofuran (THF) = | 2.4% |
| Gamma-butyrolactone (GBL) = | 0.2% |
| Butanediol (BDO) = | 91.1% |
| n-Butanol (BuOH) = | 5.5% |

Comparative Example C

4% Pd/4% Ag/8% Re on carbon—not oxidized 650 cc (276.5 gms.) of CECA ACL40 activated carbon extrudate were used as the catalyst support for this catalyst preparation. An impregnation solution was prepared by placing 139.25 gms. of Pd(NO$_3$)$_2$ soln.(7.70% Pd by wt.), 16.5 gms. of AgNO$_3$, and 41.5 gms. of HReO$_4$ solution (52.6% Re by wt.) in a 250 ml. volumetric flask along with enough acetonitrile to make the solution up to 250 ml. The solution density was 1.1846 gms./cc. 286.4 gms. of the solution was used to impregnate the 650 cc of activated carbon extrudate. Following impregnation, the catalyst preparation was allowed to stand for 5.75 hrs., then placed in an oven at 120° C. for 23 hrs. to dry. The metals loading used in this catalyst preparation per cc of carbon support were 0.016 gms. Pd/cc, 0.016 gms. Ag/cc, and 0.032 gms. Re/cc. This catalyst had the same metal loadings per volume of catalyst as the catalyst prepared in Example 3.

40 cc (21.02 gms.) of the above dried, metals-impregnated carbon catalyst preparation was loaded into a Hastelloy C reactor tube (0.745" O.D.×0.475" I.D.) and subsequently into the recycle reactor rig. The catalyst was initially reduced at 280° C. for 5 hrs. under a flowing stream of hydrogen (at atmospheric pressure). The catalyst was started up under the following conditions:

System Pressure=2500 PSIG

H2:Maleic Acid Feed Ratio=65:1

Liquid Feed Composition=400 gms. Maleic Acid/Liter

Liquid Hourly Space Velocity (LHSV)=0.55

Reactor Setpoint Temperature=180° C.

Under the above process conditions the following product selectivities were observed:

| | |
|---|---|
| Tetrahydrofuran (THF) = | 21.9% |
| Gamma-butyrolactone (GBL) = | 0.3% |
| Butanediol (BDO) = | 49.6% |
| n-Butanol (BuOH) = | 22.8% |

In order to test the inherent activity of the catalyst, the LHSV is usually increased an/or the reactor setpoint decreased until a significant increase in gamma-butyrolactone is observed in the product solution (GBL breakthrough occurs). For this catalyst, GBL breakthrough was observed at a setpoint temperature of 150° C. and an LHSV=0.55. The product selectivities observed under those conditions were as follows:

| | |
|---|---|
| Tetrahydrofuran (THF) = | 11.2% |
| Gamma-butyrolactone (GBL) = | 6.9% |
| Butanediol (BDO) = | 77.5% |
| n-Butanol (BuOH) = | 3.6% |

Example 4

5% Pd/5% Re on oxidized carbon 100 g of 30×70 mesh activated carbon (AC40, produced by CECA S.A. of France and sold in the United States by Atochem North America Inc.) was stirred with an excess of oxidizing agent (90% $HNO_3$, 30% $H_2O_2$ or 35% $HNO_3$ as set forth in Table I) at 80° C. for about 18 hours. After cooling the product was recovered by filtration and washed several times with an excess of water followed by oven drying at 120° C.

25.00 g of the oxidized carbon was treated with 120 g of an aqueous solution containing 1.90 g $NH_4ReO_4$ and 18.12 g $Pd(NO_3)_2$ solution (7.26% Pd). The resulting slurry was evaporated to dryness on a "roto-vac" and oven dried at 120° C. The product was now reduced in hydrogen at 200° C. The ramp rate was 1°/min with a hold time of 5 hours at 200° C.

8.00 g of the reduced catalyst (nominally 5% Pd/5% Re on carbon) was mixed with 100.0 g of 30% aqueous maleic acid and the mixture was placed in an autoclave. The autoclave was purged three times with 2500 psig $H_2$ at room temperature followed by an increase in the temperature to 160° C. or 180° C. as set forth in Table I at a stirring rate of 1000 rpm while maintaining the pressure at 2500 psig. The reactants were kept under those conditions for duration shown in Table I and then allowed to cool to ambient temperature. The products were analyzed by gas chromatography and showed 100% maleic conversion with selectivities 1,4-butanediol (BDO) tetrahydrofuran (THF), gamma-butyrolactone (GBL) and n-butanol as set forth in Table I.

Comparative Example D

5% Pd/5% Re on carbon—not oxidized

The procedures in Example 4 was repeated using the same activated carbon but without the oxidizing agent treatment. This catalyst was tested under conditions identical to those used in Example 4 and as set forth in Table I. The results of these tests are as set forth in Table I.

TABLE I

| Example | Oxidizing Agent | Time (hr) | T (°C.) | Selectivities | | | |
|---|---|---|---|---|---|---|---|
| | | | | BDO | THF | GBL | n-Butanol |
| Comparative Example D | None | 9.5 | 160 | 59.9 | 4.8 | 32.6 | 2.3 |
| 4 | 90% $HNO_3$ | 9.5 | 160 | 82.3 | 6.5 | 6.9 | 3.7 |

The results of Example 4 when compared with Comparative Example D show that the invention described herein (i.e. utilizing a catalyst wherein the carbon support has been contacted with an oxidizing agent as in Example 4) provides higher yields of 1,4-butanediol (BDO) with minimal gamma-butyrolactone (GBL) formation.

It is to be understood that the subject invention is not to be limited by the examples set forth herein. These have been provided merely to demonstrate operability, and the selection of catalysts, metal sources, carbon supports, concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

The invention claimed is:

1. A process for the production of 1,4-butanediol comprising catalytically hydrogenating a hydrogenatable precursor in contact with a hydrogen-containing gas and a hydrogenation catalyst comprising at least one noble metal of Group VIII of the Periodic Table and at least one of rhenium, tungsten and molybdenum deposited on a carbon support, wherein the carbon support has been contacted with an oxidizing agent selected from the group consisting of nitric acid, hydrogen peroxide, sodium hypochlorite, ammonium persulfate and perchloric acid prior to the deposition of the metals.

2. The process of claim 1 wherein the hydrogenatable precursor is selected from the group consisting of maleic acid, maleic anhydride, fumaric acid, succinic acid, succinic anhydride, dimethyl succinate, gamma-butyrolactone and mixtures thereof.

3. The process of claim 2 wherein the hydrogenatable precursor is at least one of maleic acid, succinic acid, or gamma-butyrolactone.

4. The process of claim 1 wherein the hydrogenation catalyst is prepared by the steps of (i) oxidizing the carbon support by contacting the carbon support with an oxidizing agent;

(ii) impregnating in one or more impregnation steps comprising contacting the carbon support with a source of Group VIII metal and at least one metal selected from the group consisting of rhenium, tungsten and molybdenum being in at least one solution;

(iii) drying the impregnated carbon support to remove solvent after each impregnation step; and (iv) heating the impregnated carbon support at a temperature of about 100° to 350° under reducing conditions.

5. The process of claim 1, wherein the noble metal of Group VIII is selected from the group consisting of palladium, platinum, rhodium and ruthenium.

6. The process of claim 1, wherein the hydrogenation catalyst comprises palladium and rhenium.

7. The process of claim 1, wherein the hydrogenation catalyst comprises palladium, rhenium and silver.

8. The process of claim 4, wherein the metal sources are combined into a single solution and the metals are deposited on the carbon support in a single impregnation step.

9. The process of claim 1, wherein the hydrogenation catalyst comprises about 0.1 to about 20 weight percent of the Group VIII metal and about 0.1 to about 20 weight percent of at least one of rhenium, tungsten and molybdenum.

10. The process of claim 1, wherein the ratio of hydrogen to hydrogenatable precursor is between about 5 to 1 and about 1000 to 1.

11. The process of claim 1, wherein the hydrogen-containing gas pressure is between about 20 and 400 atmospheres.

12. The process of claim 1, wherein the contact time is between about 0.1 minute and 20 hours.

13. A process for the production of tetrahydrofuran and 1,4-butanediol comprising catalytically hydrogenating a hydrogenatable precursor in contact with a hydrogenation catalyst comprising at least one noble metal of Group VIII of the Periodic Table and at least one of rhenium, tungsten, or molybdenum on an oxidized carbon support wherein the catalyst is prepared by the steps of (i) oxidizing a carbon support by contacting the carbon support with an oxidizing agent selected from the group consisting of nitric acid, hydrogen peroxide, sodium hypochlorite, ammonium persulfate and perchloric acid;

(ii) impregnating in one or more impregnation steps comprising contacting the carbon support with a source of at least one Group VIII metal and at least one metal selected from the group consisting of rhenium, tungsten or molybdenum said sources of metal being in at least one solution;

(iii) drying the impregnated carbon support to remove solvent after each impregnation step; and (iv) heating the impregnated carbon support at a temperature of about 100° C. to about 350° C. under reducing conditions.

* * * * *